(12) United States Patent
Frasca

(10) Patent No.: US 7,816,142 B1
(45) Date of Patent: Oct. 19, 2010

(54) LEAD TESTING SYSTEM

(75) Inventor: Peter Frasca, Voorhees, NJ (US)

(73) Assignee: EMSL Analytical, Inc., Westmont, NJ (US)

( * ) Notice: Subject to any disclaimer, the term of this patent is extended or adjusted under 35 U.S.C. 154(b) by 181 days.

(21) Appl. No.: 12/150,502

(22) Filed: Apr. 29, 2008

(51) Int. Cl.
*G01N 33/20* (2006.01)

(52) U.S. Cl. .......................... 436/77; 436/155; 436/177

(58) Field of Classification Search .................. 436/77, 436/155, 177; 422/100, 101, 102
See application file for complete search history.

(56) References Cited

U.S. PATENT DOCUMENTS

| | | | |
|---|---|---|---|
| 3,846,077 A | | 11/1974 | Ohringer |
| 3,955,423 A | | 5/1976 | Ohringer |
| 4,424,279 A | | 1/1984 | Bohn et al. |
| 4,458,020 A | | 7/1984 | Bohn et al. |
| 4,643,981 A | * | 2/1987 | Card .......................... 436/500 |
| 4,786,604 A | * | 11/1988 | Michael ....................... 436/77 |
| 5,019,516 A | * | 5/1991 | Wiese .......................... 436/77 |
| 5,354,652 A | * | 10/1994 | Silbergeld ..................... 435/4 |
| 5,567,619 A | | 10/1996 | Stone |
| 6,805,840 B1 | * | 10/2004 | Tajima ....................... 422/100 |
| 2005/0266585 A1 | | 12/2005 | Bargh | |

FOREIGN PATENT DOCUMENTS

| | | |
|---|---|---|
| EP | 0 294 185 | 12/1988 |
| GB | 2 392 854 | 3/2004 |
| WO | WO 90/00251 | 1/1990 |
| WO | WO 95/05598 | 2/1995 |

* cited by examiner

*Primary Examiner*—Robert J Hill, Jr.
*Assistant Examiner*—Dwan A Gerido
(74) *Attorney, Agent, or Firm*—Norman E. Lehrer

(57) ABSTRACT

A system for testing multiple samples for the presence of lead includes a plurality of vessels, a plurality of plungers, a housing for removably storing the plurality of vessels, and a retainer for holding the plurality of plungers so that each of the plungers may be inserted into a respective vessel simultaneously. In order to use the system of the present invention, a sample is placed within each of the plurality of vessels and a reagent, such as nitric acid, is added to each sample. Each sample is then heated in a separate heating device and a filtering means, such as a cotton ball, is inserted into each vessel. Each plunger then pushes its respective cotton ball into its respective vessel simultaneously so that each liquid sample is located adjacent the top of each vessel. The plungers are removed and the housing is then placed into an analyzer.

3 Claims, 3 Drawing Sheets

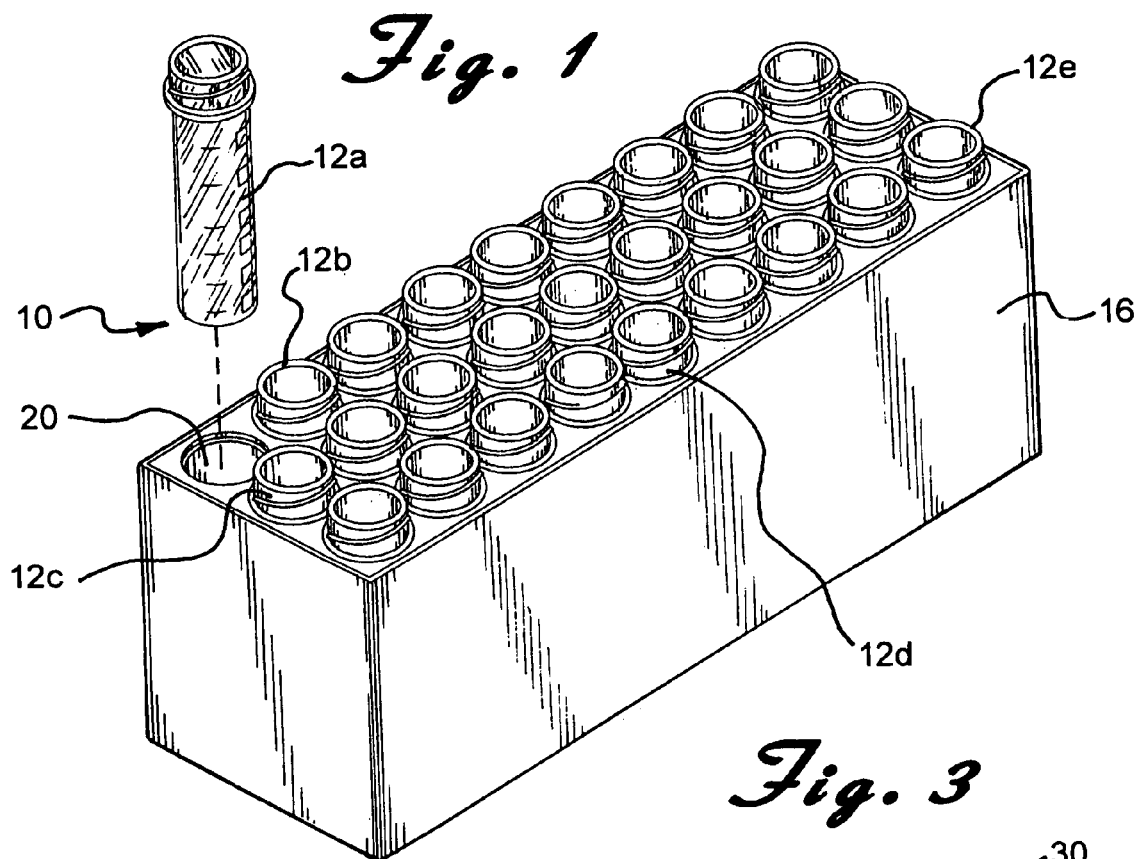
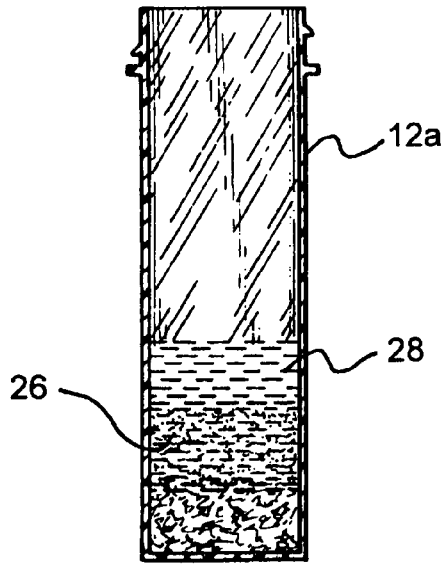
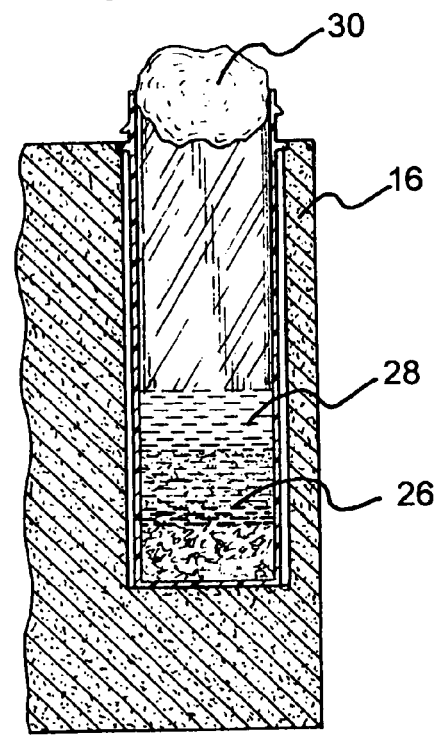

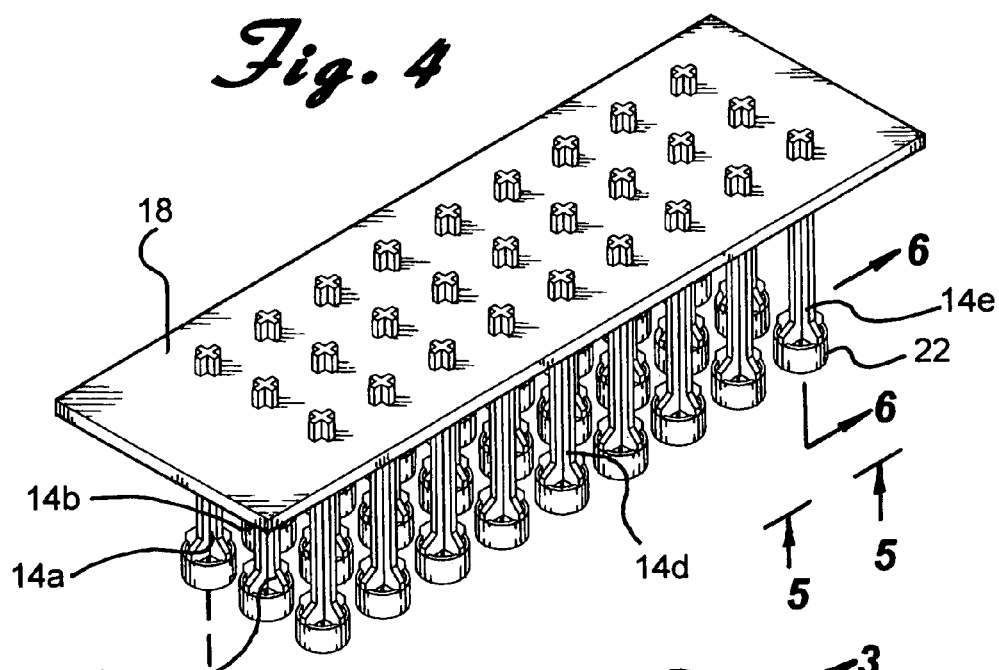
Fig. 4
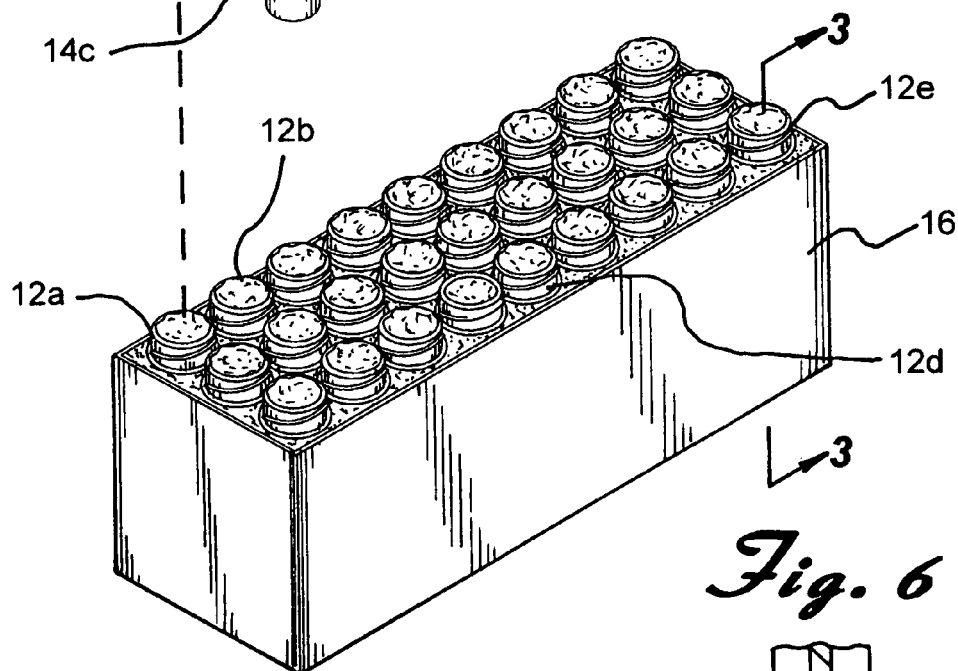
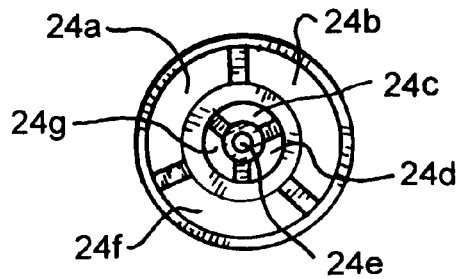
Fig. 5
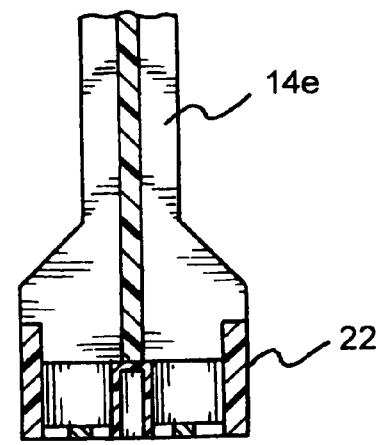
Fig. 6

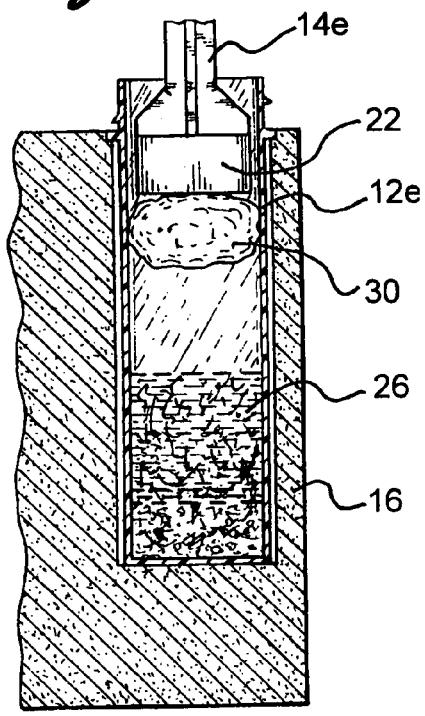
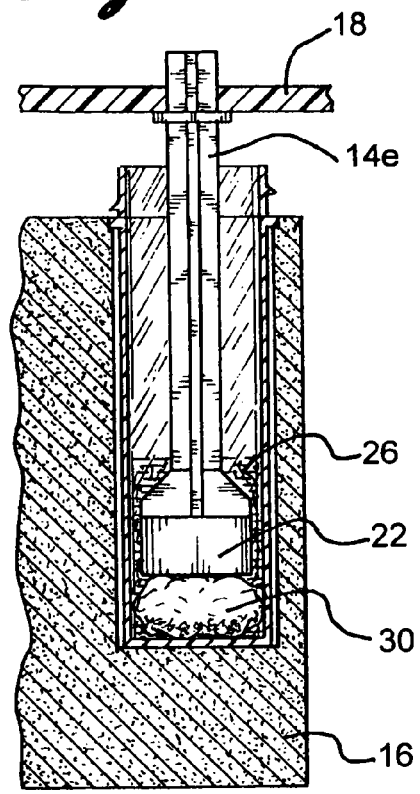
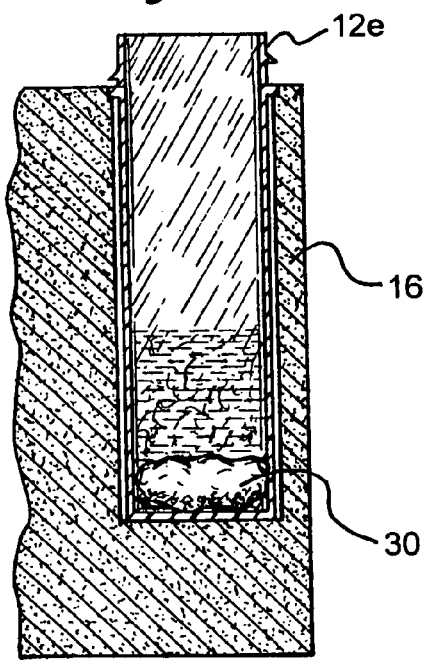
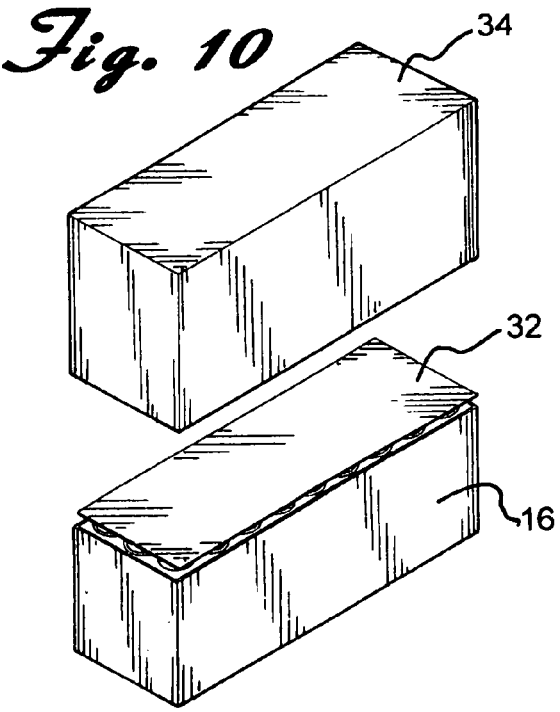

LEAD TESTING SYSTEM

BACKGROUND OF THE INVENTION

The present invention is directed toward a system for testing for the presence of lead in a sample and more particularly, toward an improved lead testing system.

Lead is a metal found naturally in the earth's crust. It can be, however, dangerous and even toxic when consumed by humans. Lead may be found in water, paint, dust, soil, and ceramics. Lead can be found in private residences as well as in many work places. Lead poisoning is pervasive and can affect every system in the human body. Lead poisoning in children especially can be fatal.

The federal government has established safe levels of lead. It is important, therefore, to have simple yet effective test methods available to individuals, as well as employers in order to provide safe environments.

Typically a lead testing system includes a vessel for collecting the test sample and preparing a liquid sample, filtering the sample, and then analyzing the sample using spectrometry. A disadvantage with this system is that the liquid sample must be extremely pure in order to avoid the spectrometer from detecting contaminants in the sample.

U.S. Pat. No. 5,567,619 to Stone discloses a process and apparatus for testing lead in a liquid sample by precipitating the lead from a liquid sample and filtering. The precipitate is contacted with a dye that forms a visible reaction when exposed to the lead. The process, however, does not appear to be as accurate as using spectrometry.

Therefore, a need exists for an accurate, simple, and efficient system for testing for the presence of lead in a sample.

SUMMARY OF THE INVENTION

The present invention is designed to overcome the deficiencies of the prior art discussed above. It is an object of the present invention to provide a system for testing for lead in a sample that is simple to conduct.

It is another object of the present invention to provide a lead testing system that is efficient and easy to use.

In accordance with the illustrative embodiments demonstrating features and advantages of the present invention, there is provided a system for testing multiple samples for lead that includes a plurality of vessels, a plurality of plungers, a housing for removably storing the plurality of vessels, and means for retaining the plurality of plungers wherein each of the plungers is inserted into a respective vessel simultaneously. In order to use the system of the present invention, a sample is placed within each of the plurality of vessels and a reagent, such as nitric acid, is added to each sample. Each sample is then heated in a separate heating device and a filtering means, such as a cotton ball, is inserted into each vessel. Each plunger then pushes its respective cotton ball into its respective vessel simultaneously so that each liquid sample is filtered adjacent the top of each vessel and any debris or other residue from the sample resides adjacent the bottom the vessel beneath the cotton ball. The plungers are then removed and the housing may be placed into an analyzer.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings one form that is presently preferred; it being understood that the invention is not intended to be limited to the precise arrangements and instrumentalities shown.

FIG. 1 is a front perspective view of the lead testing system of the present invention;

FIG. 2 is a cross-sectional view of one of the vials of the system of the present invention;

FIG. 3 is a cross-sectional view taken through line 3-3 of FIG. 4;

FIG. 4 is an exploded view of the lead testing system of the present invention;

FIG. 5 is a cross-sectional view taken through line 5-5 of FIG. 4;

FIG. 6 is a cross-sectional view taken through line 6-6 of FIG. 4;

FIG. 7 illustrates a first step in the testing system of the present invention;

FIG. 8 illustrates a second step in the testing system of the present invention;

FIG. 9 illustrates a third step in the testing system of the present invention; and FIG. 10 is a front perspective view of the system of the present invention.

DETAILED DESCRIPTION OF THE PREFERRED EMBODIMENT

Referring now to the drawings in detail wherein like reference numerals have been used throughout the various figures to designate like elements, there is shown in FIG. 1 a lead testing system constructed in accordance with the principles of the present invention and designated generally as 10.

The lead testing system of the present invention essentially includes a plurality of vessels 12a-12e, for example, a plurality of plungers 14a-14e, for example, a housing 16 for removably storing the plurality of vessels, and means for retaining 18 the plurality of plungers 14a-14e so that each of the plungers may be inserted into a respective vessel 12a-12e simultaneously as will be discussed in greater detail below.

The housing 16 may be generally rectangular and includes a plurality of openings, shown as 20, into which the plurality of vessels may be securely placed, respectively. (See FIG. 1.) The retaining means 18 may be a generally rectangular plate and includes a plurality of apertures through which an end of the body of each plunger is securely placed, respectively. (See FIG. 4.) The piston 22, for example, of each plunger extends outwardly from the retaining means. Each piston head has slots 24a-24g located therein. (See, for example, FIGS. 5 and 6.)

In order to use the system of the present invention, a sample 26 is placed within each of the plurality of vessels, for example vessel 12a, and a reagent 28, such as nitric acid, is added to the sample 26. (See FIG. 2.) Each sample is then heated in a separate heating device and a filtering means, such as a cotton ball 30, is inserted into the vessel 12a. (See FIG. 3.) Each plunger 14a, for example, then pushes its respective cotton ball into its respective vessel simultaneously, through the sample, and is then removed. (See FIGS. 7 and 8.) Each cotton ball remains adjacent the bottom of the vessel with any debris and residue from the sample residing beneath the cotton ball. The liquid of each sample has been filtered through the cotton ball and is located adjacent the top of each vessel. (See FIG. 9.) A sheet of paraffin 32 is then placed over the housing 16 and a lid 34 is then secured over the housing 16. (See FIG. 10.) The housing may then be transported to and placed into an analyzer, after removing the lid and paraffin sheet, when desired.

The housing, retaining means, the plungers, and the vessels may all be made from a plastic or similar material. The material, however, must not interfere with analyzing the samples.

The present invention may be embodied in other specific forms without departing from the spirit or essential attributes thereof and accordingly, reference should be made to the appended claims rather than to the foregoing specification as indicating the scope of the invention.

I claim:

1. A method for testing multiple samples simultaneously for lead compromising the steps of:
    providing a plurality of vessels, each of said vessels having a top and a closed bottom, a plurality of plungers, a housing for storing said plurality of vessels, and means for retaining said plurality of plungers;
    placing a sample including a liquid within each of said plurality of vessels;
    adding a reagent to each of said samples;
    heating each of said samples;
    inserting means for filtering each of said samples within each of said vessels;
    pushing each of said filtering means into its respective vessel with a respective plunger simultaneously;
    removing each of said plungers so that each of said filtering means remains adjacent the bottom of its respective vessel and said liquid resides above said filtering means; and
    placing said housing into an analyzer.

2. The method for testing samples for lead of claim 1 wherein said reagent is nitric acid.

3. The method for testing samples for lead of claim 1 wherein each of said filtering means includes a cotton ball.

* * * * *